United States Patent
Farnan

(10) Patent No.: US 8,333,727 B2
(45) Date of Patent: Dec. 18, 2012

(54) TWO PIECE ENDOVASCULAR ANASTOMOTIC CONNECTOR

(75) Inventor: Robert C. Farnan, Rivervale, NJ (US)

(73) Assignee: Circulite, Inc., Saddle Brook, NJ (US)

( * ) Notice: Subject to any disclaimer, the term of this patent is extended or adjusted under 35 U.S.C. 154(b) by 226 days.

(21) Appl. No.: 12/872,394

(22) Filed: Aug. 31, 2010

(65) Prior Publication Data

US 2011/0087063 A1    Apr. 14, 2011

Related U.S. Application Data

(60) Provisional application No. 61/249,704, filed on Oct. 8, 2009.

(51) Int. Cl.
*A61M 5/00* (2006.01)
(52) U.S. Cl. .............................................. 604/8; 600/16
(58) Field of Classification Search .............. 600/16–18; 604/8, 164.11–164.13
See application file for complete search history.

(56) References Cited

U.S. PATENT DOCUMENTS

| | | |
|---|---|---|
| 3,496,939 A | 8/1967 | Odiaga et al. |
| 3,683,926 A | 8/1972 | Suzuki |
| 4,230,119 A | 10/1980 | Blum |
| 4,503,568 A | 3/1985 | Madras |
| 4,512,761 A | 4/1985 | Raible |
| 5,443,497 A | 8/1995 | Venbrux |
| 5,449,342 A | 9/1995 | Hirose et al. |
| 5,456,712 A | 10/1995 | Maginot |
| 5,676,670 A | 10/1997 | Kim |
| 5,921,971 A | 7/1999 | Agro et al. |
| 6,019,788 A | 2/2000 | Butters et al. |
| 6,293,955 B1 | 9/2001 | Houser et al. |
| 6,428,567 B2 | 8/2002 | Wilson et al. |
| 6,468,300 B1 | 10/2002 | Freidberg |
| 6,475,232 B1 | 11/2002 | Babbs et al. |
| 6,475,234 B1 | 11/2002 | Richter et al. |
| 6,494,889 B1 | 12/2002 | Fleischman et al. |
| 6,506,202 B1 | 1/2003 | Dutta et al. |
| 6,508,836 B2 | 1/2003 | Wilson et al. |
| 6,524,334 B1 | 2/2003 | Thompson |
| 6,558,414 B2 | 5/2003 | Layne |
| 6,579,312 B2 | 6/2003 | Wilson et al. |
| 6,579,314 B1 | 6/2003 | Lombardi et al. |

(Continued)

FOREIGN PATENT DOCUMENTS

WO    2008027869 A2    3/2008

OTHER PUBLICATIONS

Atrium Medical Corp., "Atrium iCAST Covered Stent Brochure," at http://www.atriummed.com/EN/interventional/Dcouments/iCAST%20Brochure$2003603G.pdf (last visited Oct. 13, 2010).

(Continued)

*Primary Examiner* — Scott Getzow

(74) *Attorney, Agent, or Firm* — Wood, Herron & Evans, L.L.P.

(57) ABSTRACT

An anastomotic connector comprising an endovascular component including a vascular conduit and a supply conduit and a cannula component. The vascular conduit has first and second ends that are configured to reside within a vascular structure. The supply conduit has proximal and distal ends, where the distal end fluidicly connects to the vascular conduit between the first and second ends. The cannula component, which also includes proximal and distal ends, is received by the supply conduit.

31 Claims, 6 Drawing Sheets

U.S. PATENT DOCUMENTS

| | | |
|---|---|---|
| 6,585,756 B1 | 7/2003 | Strecker |
| 6,652,544 B2 | 11/2003 | Houser et al. |
| 6,669,708 B1 | 12/2003 | Nissenbaum et al. |
| 6,736,838 B1 | 5/2004 | Richter |
| 6,740,101 B2 | 5/2004 | Houser et al. |
| 6,740,115 B2 | 5/2004 | Lombardi et al. |
| 6,770,087 B2 | 8/2004 | Layne et al. |
| 6,786,920 B2 | 9/2004 | Shannon et al. |
| 6,790,225 B1 | 9/2004 | Shannon et al. |
| 6,808,533 B1 | 10/2004 | Goodwin et al. |
| 6,843,795 B1 | 1/2005 | Houser et al. |
| 6,860,899 B1 | 3/2005 | Rivelli, Jr. |
| 6,866,805 B2 | 3/2005 | Hong et al. |
| 6,875,229 B2 | 4/2005 | Wilson et al. |
| 6,887,265 B2 | 5/2005 | Richter et al. |
| 6,896,699 B2 | 5/2005 | Wilson et al. |
| 6,899,730 B1 | 5/2005 | Rivelli, Jr. |
| 6,911,040 B2 | 6/2005 | Johnson et al. |
| 6,955,688 B2 | 10/2005 | Wilson et al. |
| 6,969,395 B2 | 11/2005 | Eskuri |
| 6,979,338 B1 | 12/2005 | Loshakove et al. |
| 6,984,243 B2 | 1/2006 | Dwyer et al. |
| 6,989,071 B2 | 1/2006 | Kocur et al. |
| 6,994,713 B2 | 2/2006 | Berg et al. |
| 7,022,131 B1 | 4/2006 | Derowe et al. |
| 7,063,711 B1 | 6/2006 | Loshakove et al. |
| 7,083,640 B2 | 8/2006 | Lombardi et al. |
| 7,094,248 B2 | 8/2006 | Bachinski et al. |
| 7,108,717 B2 | 9/2006 | Freidberg |
| 7,699,864 B2 | 4/2010 | Kick et al. |
| 7,713,193 B2 | 5/2010 | Nance et al. |
| 7,722,568 B2 | 5/2010 | Lenker et al. |
| 7,780,692 B2 | 8/2010 | Nance et al. |
| 2001/0003149 A1 | 6/2001 | Utterberg et al. |
| 2002/0169495 A1 | 11/2002 | Gifford et al. |
| 2003/0195535 A1 | 10/2003 | Swanson et al. |
| 2004/0153112 A1 | 8/2004 | Nissenbaum et al. |
| 2004/0153143 A1 | 8/2004 | Quiachon et al. |
| 2005/0124937 A1 | 6/2005 | Kick et al. |
| 2005/0251187 A1 | 11/2005 | Beane et al. |
| 2006/0052750 A1 | 3/2006 | Lenker et al. |
| 2006/0135962 A1 | 6/2006 | Kick et al. |
| 2006/0135963 A1 | 6/2006 | Kick et al. |
| 2006/0135981 A1 | 6/2006 | Lenker et al. |
| 2006/0200189 A1 | 9/2006 | Nance et al. |
| 2006/0253102 A1 | 11/2006 | Nance et al. |
| 2007/0179591 A1 | 8/2007 | Baker et al. |
| 2008/0109058 A1 | 5/2008 | Greenberg et al. |
| 2008/0195125 A1 | 8/2008 | Hoffman |
| 2008/0200943 A1 | 8/2008 | Barker et al. |
| 2008/0215008 A1 | 9/2008 | Nance et al. |
| 2008/0243081 A1 | 10/2008 | Nance et al. |
| 2009/0093873 A1 | 4/2009 | Navia |
| 2009/0182188 A1 | 7/2009 | Marseille et al. |
| 2009/0287182 A1 | 11/2009 | Bishop et al. |
| 2009/0287183 A1 | 11/2009 | Bishop et al. |
| 2010/0145267 A1 | 6/2010 | Bishop et al. |
| 2010/0228077 A1 | 9/2010 | Lenker et al. |

OTHER PUBLICATIONS

Boston Scientific Corp., "Boston Scientific Announces CE Mark for SYMBIOT covered stent system: SYMBIOT II clinical trial results reported at PCR," at http://www.ptca.org/press_rel/20020528pr_boston.html (last visited Oct. 13, 2010).

Cook Medical, "Aortic Intervention," at http://www.cookmedical.com/ai/home.do (last visited Oct. 13, 2010).

Atrium Medical Corp., "FLIXENE IFG: The Best Engineered Dialysis Access Graft . . . There Can Only Be One," at http://www.atriummed.com/en/vascular/Documents/FlixenelFGX%202-sidedflyer.pdf (last visited Dec. 3, 2010).

U.S. Patent and Trademark Office, International Search Report and Written Opinion in PCT Application No. PCT/US10/048082, Oct. 25, 2010.

U.S. Patent and Trademark Office, International Search Report and Written Opinion in PCT Application No. PCT/US10/39782, Aug. 10, 2010.

United States Patent and Trademark Office, International Preliminary Report on Patentability in related International Application No. PCT/US10/039782, dated Mar. 2, 2012, 9 pp.

U.S. Patent and Trademark Office, International Preliminary Report on Patentability in PCT Application No. PCT/US10/048082, Dec. 6, 2011.

U.S. Patent and Trademark Office, "Non-final Office Action," in related U.S. Appl. No. 12/829,425 mailed Jun. 11, 2012, 10 pp.

TWO PIECE ENDOVASCULAR ANASTOMOTIC CONNECTOR

CROSS-REFERENCE TO RELATED APPLICATION

This application claims the priority of U.S. Provisional Patent Application Ser. No. 61/249,704, filed on Oct. 8, 2009 (pending), the disclosure of which is incorporated by reference herein.

TECHNICAL FIELD

The present invention relates generally to vascular connector devices and methods of using the same. More specifically, the invention relates to an anastomotic connector and a method of delivery.

BACKGROUND

The circulatory system of the human body transports blood containing chemicals, such as metabolites, hormones, and cellular waste products, to and from the cells. This organ system includes the heart, blood, and a vascular network. Veins are vessels that carry blood toward the heart while arteries carry blood away from the heart. The human heart consists of two atrial chambers and two ventricular chambers. Atrial chambers receive blood from the veins and the ventricular chambers, which include larger muscular walls, pump blood from the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and flows into the left ventricle. Finally, the blood is pumped from the left ventricle into the aorta and the vascular network.

In some instances, it becomes necessary to maintain a fluidic communication with the vascular network. For example, a circulatory assist system may be used to aid in pumping the blood through the vascular network, thereby relieving the symptoms associated with congestive heart failure (commonly referred to as heart disease). The pump of the circulatory assist system includes inflow and outflow cannulae. Often the inflow cannula connects the left atrium of the heart to the pump; the outflow cannula connects the pump to the arterial system.

Early installation of the circulatory assist device could unload the heart and prevent the further development of congestive heart failure in patients with declining left ventricular function. However, those patients who would gain the most benefit from the circulatory assist device are often too frail for the invasiveness of the surgery. Accordingly, there continues to be a need for devices and procedures that decrease the invasiveness of the surgical procedure. For example, it would be beneficial to have devices that may be delivered and secured to a vascular structure in a minimally invasive manner but that are also capable of being attached to an auxiliary device.

SUMMARY

In one illustrative embodiment, the present invention is directed to an anastomotic connector comprising a cannula component and an endovascular component including a vascular conduit and a supply conduit and a cannula component. The vascular conduit has first and second ends that are configured to reside within a vascular structure. The supply conduit has proximal and distal ends, where the distal end fluidicly connects to the vascular conduit between the first and second ends. The cannula component, which also includes proximal and distal ends, is received by the supply conduit.

In another aspect of the illustrated embodiment, the proximal end of the cannula component further includes a hub that is configured to connect to an auxiliary device.

DETAILED DESCRIPTION

Figure 1:
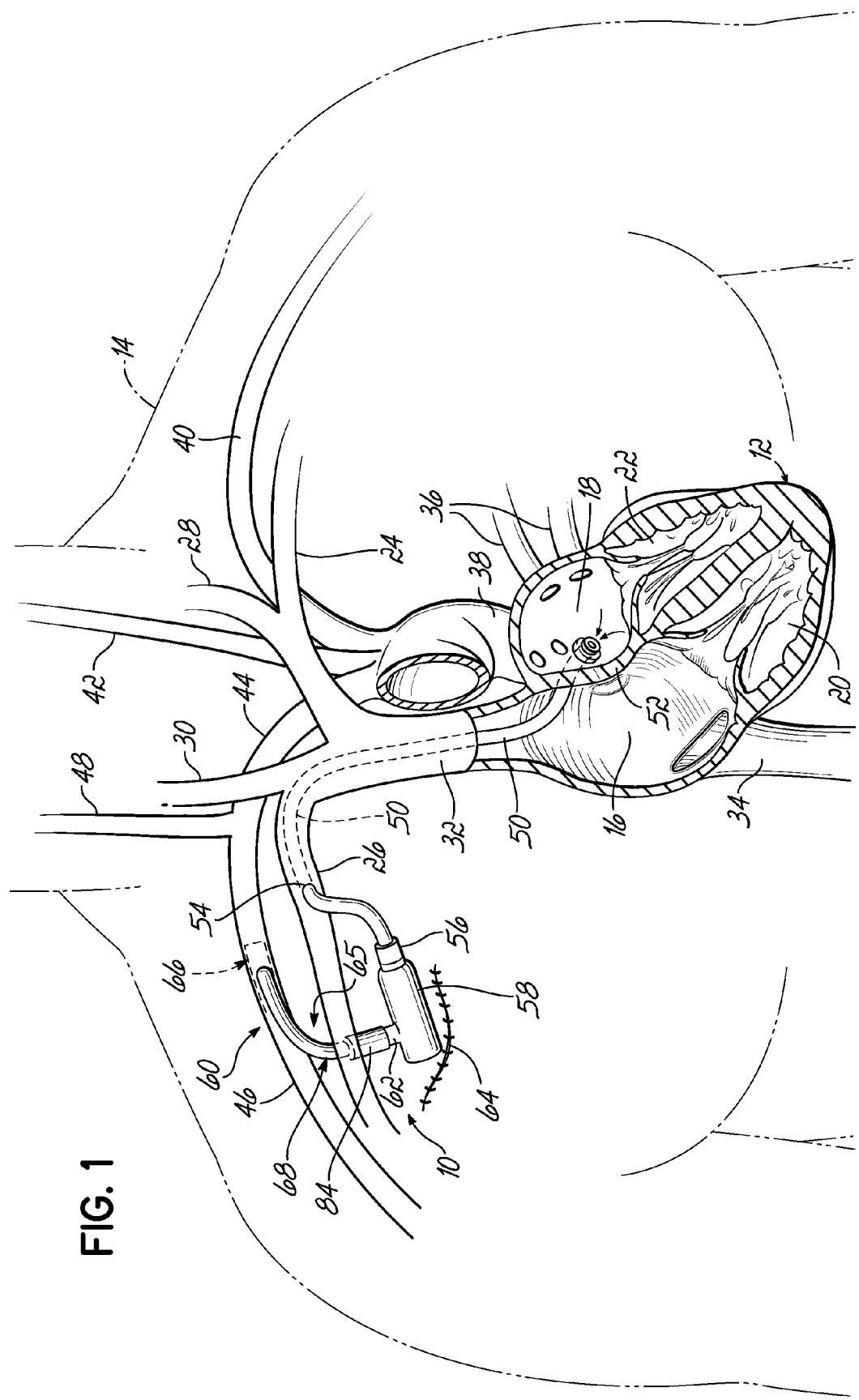
FIG. 1 is a diagrammatic view of a circulatory assist system with the outflow of the pump being connected to the right subclavian artery by an anastomotic connector, with the heart shown in cross-section.

FIG. 1 illustrates an implanted circulatory assist system 10. For illustrative purposes, certain anatomy is shown including the heart 12 of a patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 from the pulmonary veins 36 and is then pumped into the left ventricle 22. Blood leaving the left ventricle 22 enters the aorta 38 and flows into the left subclavian artery 40, the left common carotid 42, and the brachiocephalic trunk 44 including the right subclavian artery 46 and the right common carotid 48.

With respect to the implanted circulatory assist system 10, a flexible cannula body 50 extends from within the left atrium 18, through the intra-atrial septum 52, and percutaneously to a vascular access site 54 in the right subclavian vein 26. The flexible cannula body 50 is attached to an input port 56 of an implantable pump 58. An endovascular anastomotic connector 60 connects an output port 62 of the implantable pump 58 to a suitable artery, such as the right subclavian artery 46. The physician may position the implantable pump 58 subcutaneously and, optionally, submuscularly in a pump pocket 64 located near the vascular access site 54 or maintain the pump 58 externally.

Figure 2:
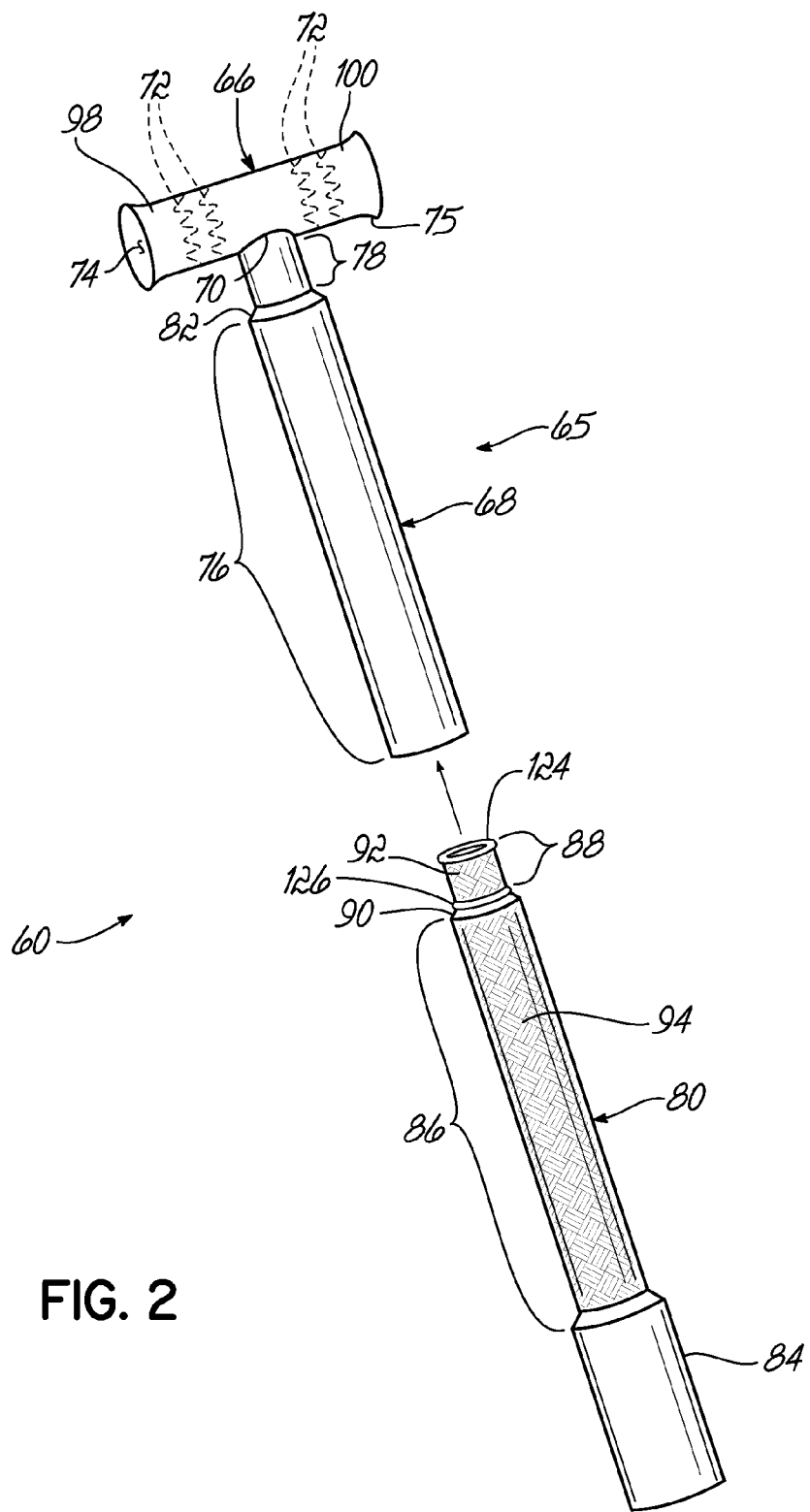
FIG. 2 is a disassembled perspective view of the anastomotic connector shown in FIG. 1.

FIG. 2 illustrates a disassembled view of the endovascular anastomotic connector 60 including an endovascular component 65 comprised of a vascular conduit 66 and a supply conduit 68 that forms a bifurcation joint 70 with the vascular conduit 66. The bifurcation joint 70 should be flexible and replicate the vessel's native compliance and forms an angle that may vary from about 5° to about 90° (perpendicular) depending on the intended use of the endovascular anastomotic connector 60 and the local anatomy.

Construction of the vascular conduit 66 may include reinforcement structures 72 of an expandable material. The expandable material may be superelastic and self-expanding, such as nickel titanium (NiTi). Alternatively, a balloon-expandable material, such as nickel cobalt (NiCo) or chromium cobalt (CrCo) may be used. The reinforcement structures 72 may then be encapsulated within a covering 74 of a porous polymeric material to allow for the migration of endothelial cells and to secure the vascular conduit 66 to the wall of the vessel. Suitable coverings may include expanded polytetrafluoroethylene (ePTFE), woven polyester, velour, or DACRON brand of synthetic polyester fabric.

Though not required, the vascular conduit 66 may be flared 75 to accommodate a wider range of vessel diameters and to provide for a smooth fluidic transition between the vascular conduit 66 and the vessel.

The supply conduit 68 may also be constructed from the porous polymeric material. In some embodiments, the wall thickness of the vascular conduit 66 may be thinner than the wall thickness of the supply conduit 68. This is more preferred over the reverse because the vascular conduit 66 is implanted within the vessel and the profile should be minimized so as to not interfere with blood flow. Yet, the walls of both the vascular and supply conduits 66, 68 should be constructed with minimal thickness to ensure flexibility in folding and delivering the endovascular component 65 in a manner described in greater detail below.

As shown, construction of the supply conduit 68 may include a major diameter section 76 and a minor diameter section 78 that is distal to the major diameter section 76. The length of the minor diameter section 78 should at least meet, or in some embodiments may slightly exceed, the wall thickness of the vessel. If the endovascular component 65 is inserted into a small volume vessel, then the minor diameter section 78 of the supply conduit 68 may be constructed to have a lumen with a diameter that is approximately equal to the diameter of the lumen of the vascular conduit 66 to constrict the volume of blood entering the vessel so as to not exceed the vessel's native capacity. The major diameter section 76 should be constructed with an inner diameter that is sufficient to receive the outer diameter of a cannula component 80 and to allow the relative movement of the same.

A transition section 82 between the major and minor diameter sections 76, 78 serves as a position stop to the cannula component 80 in a manner that is described in greater detail below.

The cannula component 80, which is directed into the supply conduit 68, provides both structural stability to the supply conduit 68 and a proximal hub 84 for connecting to the pump 58 (FIG. 1) or other auxiliary device. The cannula component 80 may be constructed from a low durometer (e.g., Shore A) material that is "soft" and has high elongation properties, such as either a thermoplastic (e.g., polyurethane or PEBAX) or a thermoset (e.g., silicone) material.

As described above with respect to the supply conduit 68, the cannula component 80 may also include major and minor diameter sections 86, 88 that are separated by a transition section 90. The major and minor diameter sections 86, 88 and the transition section 90 should be constructed with dimensions that are relative to the dimensions of the corresponding sections 76, 78, 82 of the supply conduit 68 to ensure proper and secure fit between the supply conduit 68 and the cannula component 80. The minor diameter section 88 of the cannula component 80 should also be constructed to replicate the desired angle of the bifurcation joint 70 of the endovascular component 65.

In some embodiments, the minor diameter section 88 may include a metallic support 92 constructed from NiTi, stainless steel, or other similar biocompatible metal. The metallic support 92 aids in preventing the minor diameter section 88 from collapsing due to external forces applied as the cannula component 80 is fit with the supply conduit 68. The metallic support 92 may be formed as a braid (as shown in FIG. 2) or coil (as shown in FIG. 3F) that is encapsulated within the porous polymeric material comprising the wall of the minor diameter section 88. The major diameter section 86 may also be supported by a metallic support 94 that is constructed in a similar manner and provides kink resistance.

The hub 84 of the cannula component 80 extends proximally from the supply conduit 68 and may vary in length such that the physician may adjust the overall length of the endovascular anastomotic connector 60 to fit a particular individual's anatomy. One manner of constructing an adjustable hub 84 includes molding annular members (not shown) that are longitudinally spaced. The longitudinal spacing may be sufficient to accommodate the outlet 62 (FIG. 1) of the pump 58 (FIG. 1). Accordingly, the physician may cut the hub 84 at an appropriate length and between successive annular members.

FIGS. 3A-3F illustrate one exemplary manner to use the endovascular anastomotic connector 60. In preparing for the method, the physician preloads the endovascular component 65 into a delivery system 95, which as shown includes a delivery sheath 96 and a delivery catheter 97. One exemplary manner of folding includes wrapping a first end 98 of the vascular conduit 66 around the supply conduit 68 after the delivery catheter 97 is directed through the supply conduit 68 and distally out from a second end 100 of the vascular conduit 66. The wrapped endovascular anastomotic connector 60 with the delivery catheter 97 are then loaded into the delivery sheath 96. In some embodiments, though not specifically shown, the delivery catheter 97 may include a balloon portion that is at least slightly inflated so as to contact an inner surface of the vascular conduit 66 and to aid in stabilizing the position of the endovascular component 65 during delivery.

Figure 3A:
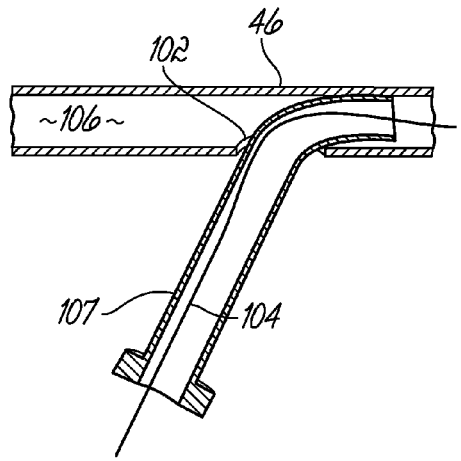
FIGS. 3A-3C are diagrammatic views, in partial cross-section, illustrating successive steps of one exemplary procedure for implanting an endovascular component of the anastomotic connector into the right subclavian artery.

In the illustrative manner of using the endovascular anastomotic connector 60, FIG. 3A shows an incision 102 in the wall of the vessel, illustrated here as the right subclavian artery 46. The physician then advances a guide-wire 104 through the incision 102 and into the lumen 106 of the right subclavian artery 46. An introducer 107 is backloaded over the guide-wire 104 to maintain access into the artery 46 through the incision 102 while reducing or preventing bleeding. Suitable introducers may include those that are commercially available, such as the CHECK-FLO PERFORMER by Cook Medical, Bloomington, IN, or may be customized to a particular need.

Figure 3B:
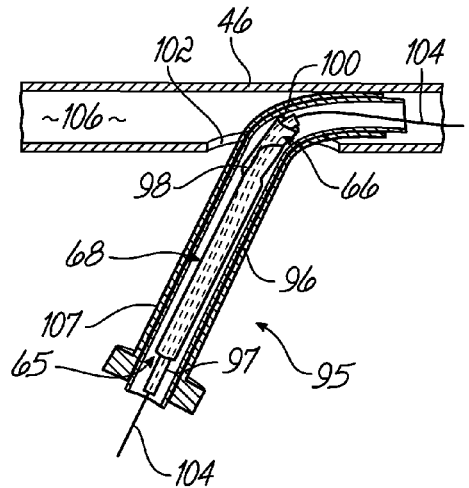

In FIG. 3B, the folded endovascular component 65 with the delivery system 95 are then back-loaded over the guide-wire 104, advanced through the introducer 107 and into the artery 46 until the delivery sheath 96 is positioned just distal to a distal end of the introducer 107. The guide-wire 104 extends coaxially through the lumen of the delivery catheter 97.

With the delivery sheath 96 and the endovascular component 65 properly positioned, the physician may partially retract the delivery sheath 96 to release and deploy the second end 100 of the vascular conduit 66. Continued retraction will then release and deploy the first end 98 of the vascular conduit 66. Alternatively, the physician can advance the delivery catheter 97 with the endovascular component 65 distally from the delivery sheath 96 and into the lumen 106 of the artery 46.

Figure 3C:
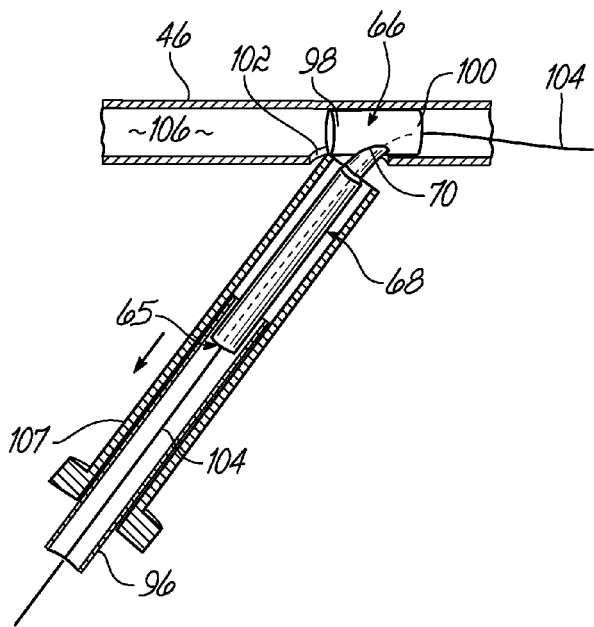

FIG. 3C illustrates the deployed vascular conduit 66 within the lumen 106 of the right subclavian artery 46. In those embodiments where the reinforcement structures 72 (FIG. 2) are constructed from a self-expanding material, the vascular conduit 66 would automatically expand to fill the volume of the lumen 106 of the right subclavian artery 46 once unconstrained. FIG. 3C further illustrates a bifurcation joint having an angle that is less than 90°.

The position of the vascular conduit 66 within the right subclavian artery 46 may be manipulated by moving the delivery sheath 96, the supply conduit 68, and/or the delivery catheter 97 to ensure that the vascular conduit 66 creates a seal against the incision 102. The delivery sheath 96 and delivery catheter 97 are then retracted from the endovascular component 65 while the introducer 107 and the guide-wire 104 may remain as positioned.

In those embodiments where the vascular conduit 66 is constructed from a balloon-expandable material, a conventional balloon catheter 108 (FIG. 3D) may then be used to expand the vascular conduit 66 in a manner described with reference to FIGS. 3D-3F.

Figure 3D:
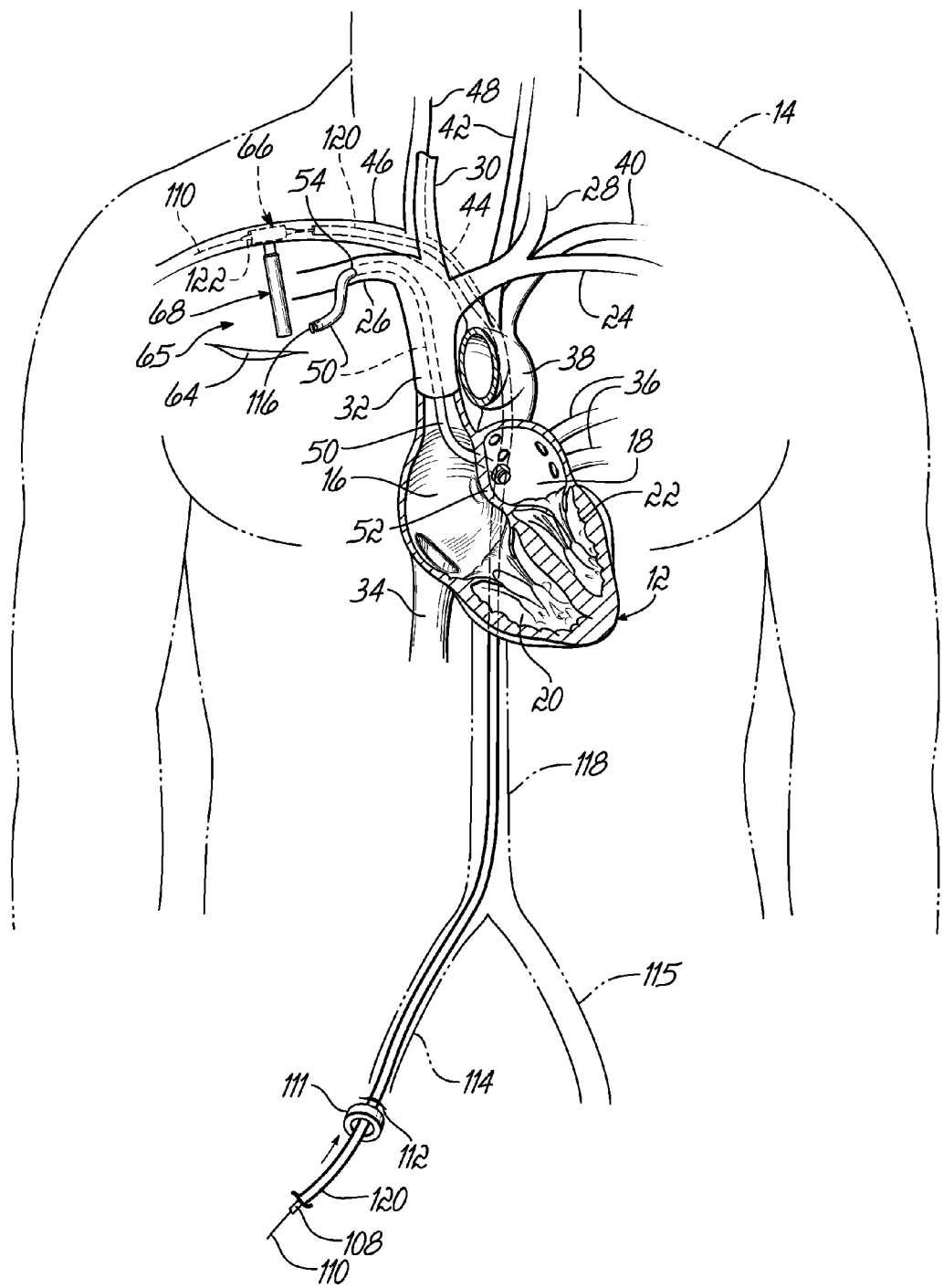
FIG. 3D is a diagrammatic view of one manner of directing a balloon catheter from a secondary incision site to the endovascular component of the anastomotic connector.
Figure 3E:
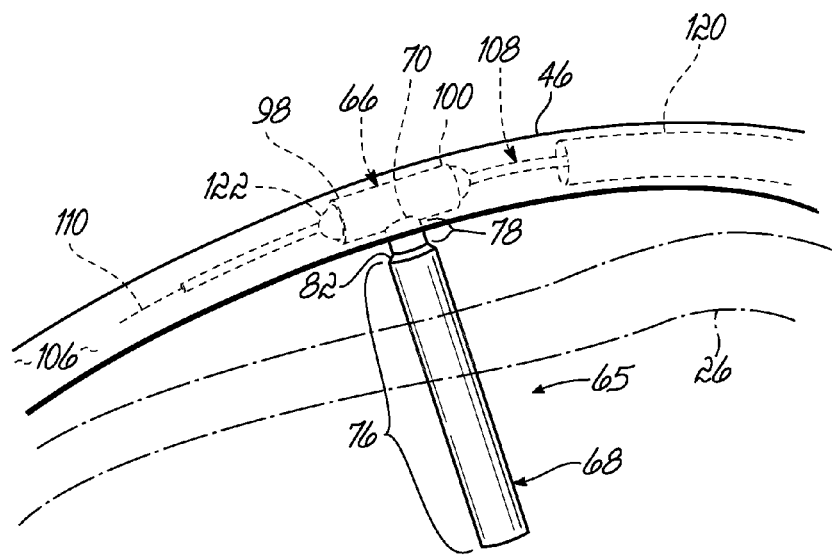
FIG. 3E is a diagrammatic view, in partial cross-section, illustrating the balloon-assisted expansion of a vascular conduit.
Figure 3F:
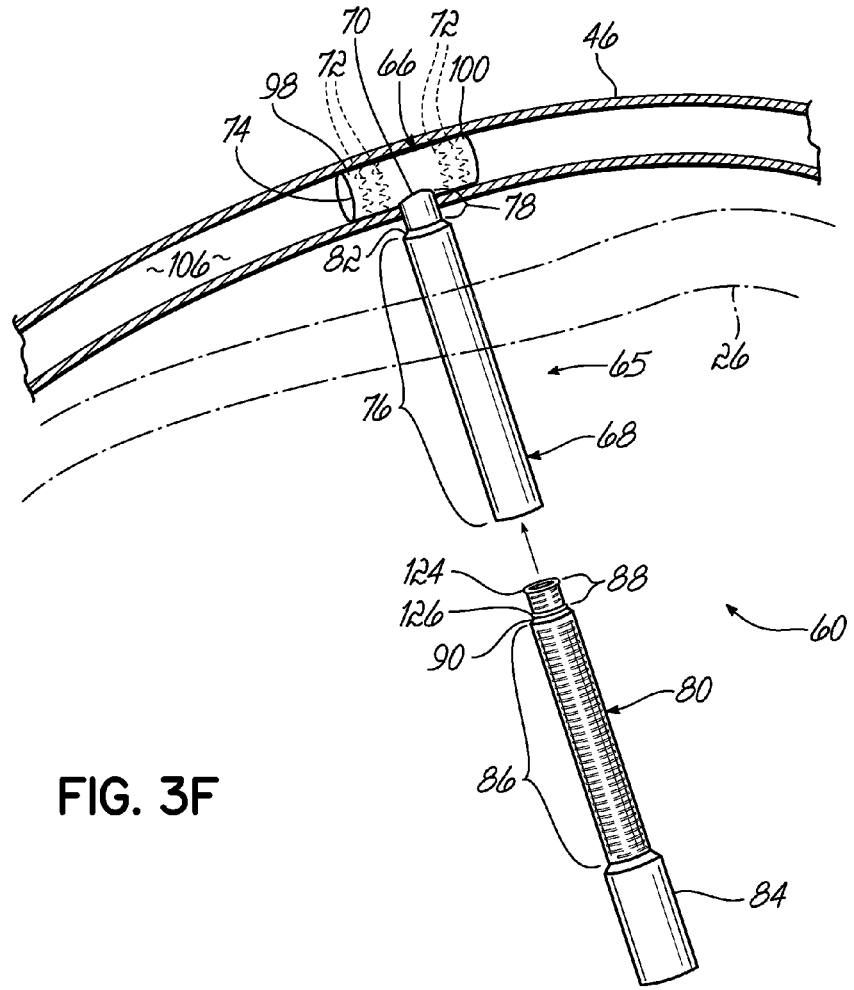
FIG. 3F is a diagrammatic view of the insertion of a cannula component into the supply conduit of the endovascular component.

FIG. 3D illustrates the directing of the balloon catheter 108 along a second guide-wire 110 through an introducer 111 positioned at a secondary incision site 112 and to the lumen of the vascular conduit 66. The introducer 111 may be similar to the introducer 107 (FIG. 3A) described previously. As shown, the secondary incision site 112 may be located at the right or left femoral artery 114, 115 and is proximate to a femoral vein access site (not shown) that was used in percutaneously accessing the intra-atrial septum 52 (FIG. 1) for implanting the transseptal flexible cannula body 50. One manner of percutaneously accessing and implanting is described in greater detail in U.S. application Ser. No. 12/256,911, the disclosure of which is incorporated in its entirety herein by reference. A plug 116 may be temporarily positioned in the proximal end of the flexible cannula body 50 to prevent loss of blood and until the flexible cannula body 50 is fluidicly connected to the pump 58 (FIG. 1).

The second guide-wire 110 is directed from the secondary incision site 112, up the descending aorta 118, through the brachiocephalic trunk 44, and into the right subclavian artery 46. A guide catheter 120 may then be directed over the second guide-wire 110 to a position just before the vascular conduit 66. The balloon catheter 108 is then advanced over the second guide-wire 110 and through the guide catheter 120 until it extends distally from the guide catheter 120 and such that its balloon portion 122 resides within the lumen of the vascular conduit 66, as shown in FIG. 3E.

With the balloon catheter 108 appropriately positioned, the physician may then inflate the balloon portion 122, which will contact the inner surface of the vascular conduit 66 and cause the reinforcement structures 72 (FIG. 2) to expand. As a result, the vascular conduit 66 fills the lumen 106 (FIG. 3A) of the right subclavian artery 46. The balloon portion 122 of the balloon catheter 108 may then be deflated and retracted from the endovascular component 65. The guide catheter 120 and the second guide-wire 110 may also be retracted.

Though not specifically shown, an alternate manner of directing the balloon catheter 108 may be from, for example, an incision near the right radial artery, or any other vascular structure that provides accessibility to the endovascular component 65.

FIG. 3F then illustrates the advancing of the cannula component 80 into the supply conduit 68 of the endovascular anastomotic connector 60. The cannula component 80 is advanced until the transition section 90 makes contact with and seats on the transition section 82 of the supply conduit 68, which creates a positive stop to the cannula component 80.

Figure 4:
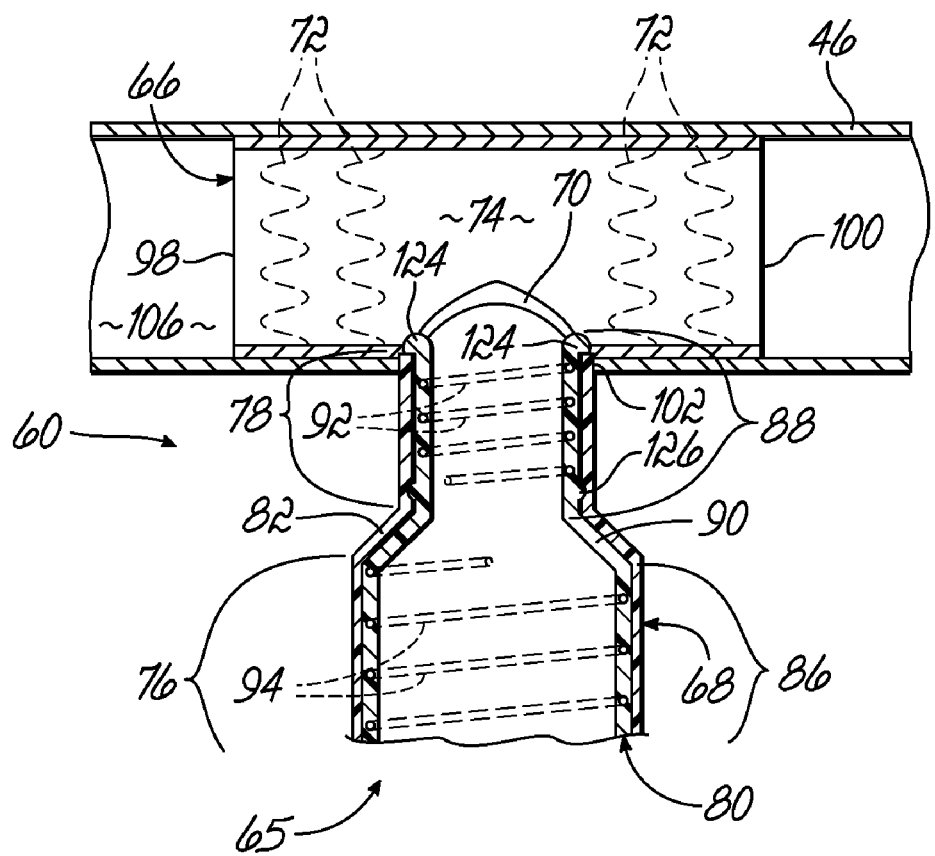
FIG. 4 is an enlarged diagrammatic view, in cross-section, of the endovascular anastomotic connector implanted in the right subclavian artery.

FIG. 4 illustrates the interference fit between the cannula component 80 and the supply conduit 68 by one or more seal rings in the assembled device. As shown, the minor diameter section 88 of the cannula component 80 includes a distal seal ring 124 and a proximal seal ring 126. The proximal seal ring 126 may provide an interference fit between the supply conduit 68 and the cannula component 80. The distal seal ring 124 provides an interference fit at the bifurcation joint 70 to ensure a smooth fluidic transition between the vascular conduit 66 and the cannula component 80. As the minor diameter section 88 of the cannula component 80 slides into the minor diameter section 78 of the supply conduit 68, the wall of the right subclavian artery 46 is stretched by the distal seal ring 124. This stretching aids in sealing the endovascular anastomotic connector 60 at the incision 102 by radial compression.

The physician may complete the procedure by cutting the hub 84 (FIG. 2) to an appropriate length and connecting it to the outflow port 62 (FIG. 1) of the pump 58 (FIG. 1). The plug 116 (FIG. 3D) is removed from the proximal end of the flexible cannula body 50 (FIG. 1), such that the flexible cannula body 50 (FIG. 1) may be connected to the inflow port 56 (FIG. 1) of the pump 58 (FIG. 1).

As was shown in FIG. 1, the completed flow of blood will be as follows: oxygenated blood will travel from the left atrium 18 via the natural path into the left ventricle 22 to the aorta 38. From the aorta 38, blood moves into the left subclavian artery 40, the left common carotid 42, and the brachiocephalic trunk 44. Oxygenated blood will also enter the flexible cannula body 50 from the left atrium 18 and travel through the lumen of the flexible cannula body 50 to the pump 58. The pump 58 actively pumps blood into the cannula component 80 of the endovascular anastomotic connector 60 and into the right subclavian artery 46. From here, the blood is directed into the remainder of the vascular network.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. An anastomotic connector comprising:
   (i) an endovascular component comprising:
      a vascular conduit including first and second ends and a lumen extending therebetween, wherein the vascular conduit is configured to be inserted through an incision in an existing vascular structure and reside within the existing vascular structure; and
      a supply conduit having a proximal end, a distal end, a lumen extending therebetween, and wherein the distal end of the supply conduit forms a bifurcation joint with the vascular conduit and fluidicly connects to the lumen of the vascular conduit between the first and second ends; and (ii) a cannula component having a proximal end, a distal end, a lumen extending therebetween, and a seal ring at the distal end, wherein the cannula component is adapted to be received by the supply conduit and extend proximally therefrom and wherein the seal ring expands to seal the incision in the existing vascular structure at the bifurcation joint when the cannula component is engaged with the supply conduit.

2. The anastomotic connector of claim 1, further comprising:
a hub coupled to the proximal end of the cannula component, the hub being configured to connect to an auxiliary device.

3. The anastomotic connector of claim 2, wherein a length of the hub is adjustable.

4. The anastomotic connector of claim 2, wherein the auxiliary device is an implantable pump.

5. The anastomotic connector of claim 1, wherein the first and second ends of the vascular conduit include reinforcement structures.

6. The anastomotic connector of claim 5, wherein the reinforcement structures are constructed from a self expanding material.

7. The anastomotic connector of claim 5, wherein the reinforcement structures are constructed from a balloon-expanding material.

8. The anastomotic connector of claim 5, wherein the reinforcement structures are encapsulated in a porous polymeric biomaterial capable of promoting tissue in-growth.

9. The anastomotic connector of claim 1, wherein the first and second ends of the vascular conduit are flared.

10. The anastomotic connector of claim 1, wherein the supply conduit further comprises:
a major diameter section; and
a minor diameter section, wherein the minor diameter section is distal to the major diameter section.

11. The anastomotic connector of claim 10, wherein a transition section couples the larger major diameter section to the smaller minor diameter section when the anastomotic connector is directed into the existing vascular structure having an inner diameter that is smaller than a diameter of the major diameter section.

12. The anastomotic connector of claim 11, wherein the transition section provides a positive stop to the cannula component.

13. The anastomotic connector of claim 12, wherein a transition section of the cannula component couples the larger major diameter section of the cannula component to the smaller minor diameter section of the cannula component.

14. The anastomotic connector of claim 13, wherein the transition section of the cannula component is received by a transition section of the supply conduit, wherein the transition section of the supply conduit couples the larger major diameter section of the supply conduit to the smaller minor diameter section of the supply conduit.

15. The anastomotic connector of claim 10, wherein a diameter of a lumen of the minor diameter section is substantially similar to a diameter of the lumen of the vascular conduit.

16. The anastomotic connector of claim 10, wherein a length of the minor diameter section is equal to or exceeds a wall thickness of the existing vascular structure.

17. The anastomotic connector of claim 10, wherein the cannula component further comprises:
a major diameter section received by the major diameter section of the supply conduit; and
a minor diameter section, wherein the minor diameter section is distal to the major diameter section and the minor diameter section is received by the minor diameter section of the supply conduit.

18. The anastomotic connector of claim 17, wherein the minor diameter section includes at least one seal ring creating a fluidic seal by interference fit with the minor diameter of the supply conduit.

19. The anastomotic connector of claim 18, wherein the endovascular component is configured to be collapsible so as to be loaded into a delivery system and to move relative thereto.

20. The anastomotic connector of claim 19, wherein the delivery system includes a delivery catheter that is directed through the endovascular component and a delivery sheath that receives the delivery catheter and the endovascular component.

21. The anastomotic connector of claim 1, wherein the supply conduit is constructed from a porous polymeric biomaterial capable of promoting tissue in-growth.

22. The anastomotic connector of claim 1, wherein the cannula component includes a metallic support in a wall of the cannula component.

23. The anastomotic connector of claim 22, wherein the metallic support is a coil or a braid.

24. The anastomotic connector of claim 1, wherein the cannula component is constructed from a thermoplastic or a thermoset material.

25. The anastomotic connector of claim 1, wherein a diameter of the vascular conduit is substantially similar to a diameter of the vascular structure.

26. A method of connecting an auxiliary device to an existing vascular structure with an anastomotic connector, the anastomotic connector comprising:
(a) an endovascular component comprising a vascular conduit having first and second ends and a lumen extending therebetween, wherein the vascular conduit is configured to be inserted through an incision in the existing vascular structure and reside within the existing vascular structure and a supply conduit having a proximal end, a distal end, and a lumen extending therebetween, wherein the distal end of the supply conduit forms a bifurcation joint with the vascular conduit and fluidicly connects to the lumen of the vascular conduit between the first and second ends; and
(b) a cannula component having a proximal end, a distal end, and a lumen extending therebetween, wherein the cannula component is adapted to be received by the supply conduit and extend proximally therefrom, a seal ring at the distal end of the cannula component, and a hub coupled to the proximal end of the cannula component the hub being configured to connect to the auxiliary device, the method comprising:
(i) advancing the endovascular component into the vascular structure;
(ii) deploying the first and second ends of the vascular conduit within the vascular structure;
(iii) deploying the supply conduit;
(iv) advancing the cannula component into the supply conduit of the endovascular component thereby expanding the seal ring and sealing the incision at the bifurcation joint; and
(v) coupling the hub of the cannula component to the auxiliary device.

27. The method according to claim 26 further comprising:
adjusting a length of the hub of the cannula component before coupling the hub to the auxiliary device.

28. The method according to claim 26 further comprising: sealing the vascular conduit against an incision in the vascular structure by manipulating the endovascular component before deploying the supply conduit.

29. The method according to claim 26, wherein the first and second ends of the vascular conduit include reinforcement structures.

30. The method according to claim 29 further comprising: advancing a balloon catheter into the vascular conduit before advancing the cannula component;
inflating a balloon portion of the balloon catheter to expand the reinforcement structures; and
retracting the balloon catheter.

31. A method of connecting an auxiliary device to an existing vascular structure with an anastomotic connector, the anastomotic connector comprising:
(a) an endovascular component comprising a vascular conduit having first and second ends and a lumen extending therebetween, wherein the vascular conduit is configured to be inserted through an incision in the existing vascular structure and reside within the vascular structure and a supply conduit having a proximal end, a distal end, and a lumen extending therebetween, wherein the distal end of the supply conduit forms a bifurcation joint with the vascular conduit and fluidicly connects to the lumen of the vascular conduit between the first and second ends; and
(b) a cannula component having a proximal end, a distal end, and a lumen extending therebetween, wherein the cannula component is adapted to be received by the supply conduit and extend proximally therefrom, a seal ring at the distal end of the cannula component, and a hub coupled to the proximal end of the cannula component, the hub being configured to connect to the auxiliary device, the method comprising:
(i) creating an incision in the vascular structure;
(ii) loading the endovascular component into a delivery system;
(iii) directing a guide-wire into the vascular structure and then advancing an introducer over the guide-wire to maintain the incision;
(iv) advancing the endovascular component with the delivery system over the guide-wire and into the vascular structure;
(v) deploying the first and second ends of the vascular conduit within the vascular structure;
(vi) sealing the incision with the endovascular component;
(vii) deploying the supply conduit;
(viii) advancing the cannula component into the supply conduit thereby expanding the seal ring and sealing the incision at the bifurcation joint;
(ix) retracting the introducer and the guide-wire from the incision; and
(x) coupling the hub of the cannula component to the auxiliary device.

* * * * *